(12) United States Patent
Boroczky et al.

(10) Patent No.: US 10,504,197 B2
(45) Date of Patent: Dec. 10, 2019

(54) CLINICAL DECISION SUPPORT SYSTEMS AND METHODS

(75) Inventors: Lilla Boroczky, Mount Kisco, NY (US); Ye Xu, Hartsdale, NY (US); Jeremy Drysdale, Tarrytown, NY (US); Michael Chun-chieh Lee, Bronx, NY (US); Lina Arbash Meinel, Homewood, IL (US); Thomas Buelow, Grosshansdorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 956 days.

(21) Appl. No.: 13/264,657

(22) PCT Filed: Mar. 9, 2010

(86) PCT No.: PCT/IB2010/051013
§ 371 (c)(1),
(2), (4) Date: Oct. 14, 2011

(87) PCT Pub. No.: WO2010/119356
PCT Pub. Date: Oct. 21, 2010

(65) Prior Publication Data
US 2012/0041779 A1    Feb. 16, 2012

Related U.S. Application Data

(60) Provisional application No. 61/169,473, filed on Apr. 15, 2009.

(51) Int. Cl.
*G16H 40/20*    (2018.01)
*G16H 50/20*    (2018.01)
(Continued)

(52) U.S. Cl.
CPC ............. *G06Q 50/22* (2013.01); *G06F 19/00* (2013.01); *G16H 40/63* (2018.01); *G16H 50/20* (2018.01); *G06F 19/321* (2013.01)

(58) Field of Classification Search
CPC ... G06Q 50/22; G06F 19/3406; G06F 19/345; G06F 19/321; G16H 10/60; G16H 15/00;
(Continued)

(56) References Cited

U.S. PATENT DOCUMENTS 8,607,148 B2 * 12/2013 Singh et al. .................. 715/764
2003/0013951 A1    1/2003 Stefanescu et al.
(Continued)

FOREIGN PATENT DOCUMENTS

CN    101346722 A    1/2009
JP    2006146623 A    6/2006
(Continued)

OTHER PUBLICATIONS

W. Horsthemke et al, ."Task-Oriented Medical Image Retrieval" , MICCAI'07 Content-based Image Retrieval Workshop, Brisbane, Australia, Oct. 2007. Document Horsthemke.pdf attached. [Case based and evidence based retrieval]; pp. 1-10.
(Continued)

*Primary Examiner* — Hiep V Nguyen

(57) ABSTRACT

A clinical decision support (CDS) system comprises: a case grouping sub-system (10) including a graphical user interface (30) that is operative to simultaneously display data representing a plurality of patient cases and further configured to enable a user to group selected patient cases represented by the simultaneously displayed data into clinically related groups (32) as selected by the user; a probative features determination sub-system (12) that is operative to determine probative features (44) that correlate with the clinically related groups; and a CDS user interface (16) that
(Continued)

Figure 1:
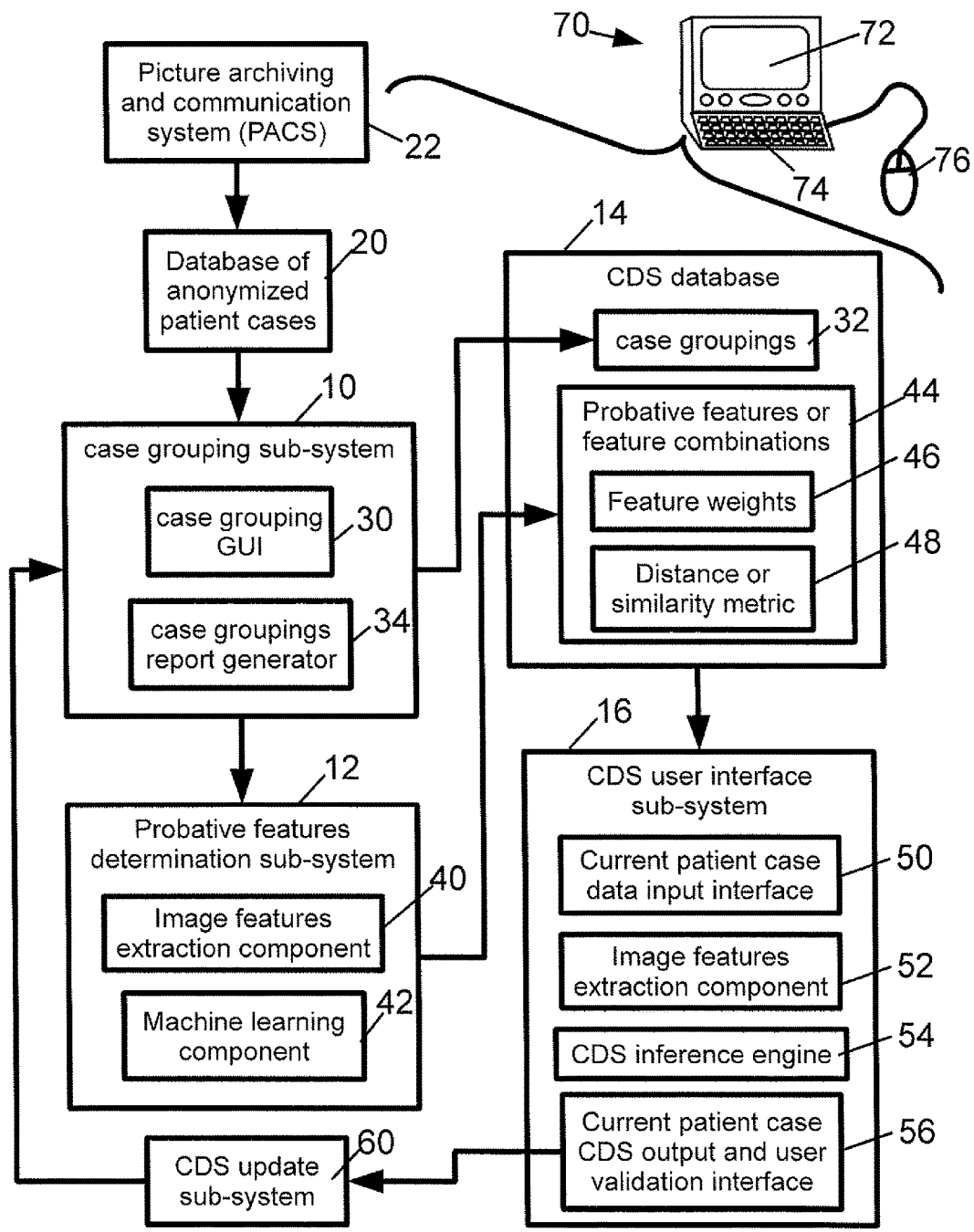

is operative to receive current patient data relating to a current patient case and to output clinical decision support information based on values of the probative features determined from the received current patient data.

20 Claims, 4 Drawing Sheets

(51) Int. Cl.
*G06Q 50/22* (2018.01)
*G16H 40/63* (2018.01)
*G06F 19/00* (2018.01)

(58) Field of Classification Search
CPC ........ G16H 50/20; G16H 10/40; G16H 30/20; G16H 40/20; G16H 40/63
USPC .......................................................... 705/2
See application file for complete search history.

(56) References Cited

U.S. PATENT DOCUMENTS

| | | | |
|---|---|---|---|
| 2003/0195883 A1* | 10/2003 | Mojsilovic et al. | 707/6 |
| 2005/0261941 A1 | 11/2005 | Scarlat | |
| 2006/0231108 A1 | 10/2006 | Novatzky et al. | |
| 2007/0175980 A1 | 8/2007 | Alsafadi | |
| 2008/0095418 A1* | 4/2008 | Moriya | 382/128 |
| 2008/0192995 A1 | 8/2008 | Zhao | |
| 2008/0298766 A1 | 12/2008 | Wen et al. | |
| 2009/0138432 A1 | 5/2009 | Agnihotri et al. | |
| 2011/0166879 A1* | 7/2011 | Lee | G06F 19/3443 705/2 |
| 2011/0191343 A1* | 8/2011 | Heaton et al. | 707/737 |
| 2012/0041779 A1 | 2/2012 | Boroczky et al. | |

FOREIGN PATENT DOCUMENTS

| | | |
|---|---|---|
| JP | 2007061638 A | 3/2007 |
| JP | 2007279942 A | 10/2007 |
| JP | 2008188096 A | 8/2008 |

OTHER PUBLICATIONS

D. S. Raicu et al, "Modeloing Semantics From Image Data: Opportunities From LIDC" from facweb.cs.depaul.edu Special issue "Warehousing and Mining Complex Data: Applications to Biology, Medicine, Behavior, Health and Environment" of the International Journal of Biomedical Engineering, vol. 2, (3), 2009. Document raicu.pdf is attached. pp. 1-22.

Tourassi et al.; "Computer-Assisted Detection of Mammographic Masses" in Medical Physics, vol. 30, No. 8, Aug. 2003, pp. 2123-2130.

Li, Q. et al. "Investigation of new psychophysical measures for evaluation of similar images on thoracic computed tomography for distinction between benign and malignant nodules". Medical Physics, 2003, 30(10), 2584-2593.

* cited by examiner

CLINICAL DECISION SUPPORT SYSTEMS AND METHODS

The following relates to the medical arts, medical diagnostic arts, medical case management arts, expert system arts, and related arts.

Clinical decision support (CDS) systems are expert systems constructed to provide automated assistance to physicians or other medical personnel in making medical decisions such as ailment diagnosis, treatment selection, implementation of aspects of a treatment regimen, and so forth. Some illustrative CDS systems are described, for example, in Alsafadi, U.S. Publ. Appl. No. 2007/0175980 A1.

In conventional or "manual" clinical diagnosis, case results from a physician's own experience guide the physician's decisions regarding new clinical situations. A case-based CDS system attempts to emulate this approach by facilitating automated access to a voluminous set of past cases that exceeds the historical experience possessed by any single physician. For example, a case-based CDS system can provide decision support for diagnosing an abnormality found in breast cancer studies of a patient by retrieving test results and other relevant information from past patient cases (with the patient data suitably anonymized to comply with patient privacy regulations or standards). Such case-based CDS systems emulate clinical decision-making thought processes that are generally accepted as proper in the medical arts. In effect, the CDS system operates as an information retrieval system which retrieves similar past medical cases, and may also retrieve or particularly identify relevant medical test results or other case information that is likely to be probative for a present diagnosis or other present medical decision.

Known case-based CDS systems for automated decision-making employ various techniques to identify similar cases. In image retrieval, for example, pairwise comparison of image features is sometimes used to identify similar images. However, such approaches do not readily distinguish the "weights" or significance placed on the various image features in quantifying similarity or dissimilarity of the images. Moreover, if such pairwise comparisons are done manually, experimental or individual bias can be introduced due to the small and limited "sampling set" of two compared items.

Various machine learning approaches have also been used in information retrieval systems in order to automatically group similar objects based on automated analysis of object features. Again, however, machine learning does not readily provide information as to the basis by which similarity or dissimilarity is assessed. The machine learned algorithm is a "black box" that may be suitable for applications such as image retrieval—but, a physician or other medical person is unlikely to be comfortable with making a medical diagnosis or other medical decision on an empirical basis without understanding the underlying decision-making rationale.

Relevance feedback techniques are also known. In these techniques, human-performed or other authoritative analysis is applied to information retrieval results to assess the actual relevance of the retrieved information. These authoritative assessments are used to refine the information retrieval algorithm in the hope of improving subsequent retrieval operations. A difficulty with relevance feedback in the CDS context is that feedback over time is likely to come from different physicians, potentially resulting in differing or contradictory relevance feedback. Additionally, relevance feedback requires time to assess the retrieved results and provide the feedback, which a busy physician may be unwilling to do. Still further, relevance feedback only provides refinement for an existing information retrieval system and does not provide a basis for constructing a CDS system ab initio.

The following provides new and improved apparatuses and methods which overcome the above-referenced problems and others.

In accordance with one disclosed aspect, a clinical decision support (CDS) system comprises: a case grouping sub-system including a graphical user interface that is operative to simultaneously display data representing a plurality of patient cases and further configured to enable a user to group selected patient cases represented by the simultaneously displayed data into clinically related groups as selected by the user; a probative features determination sub-system that is operative to determine probative features that correlate with the clinically related groups; and a CDS user interface that is operative to receive current patient data relating to a current patient case and to output clinical decision support information based on values of the probative features determined from the received current patient data.

In accordance with another disclosed aspect, a clinical decision support (CDS) method implemented by a CDS system is disclosed, the CDS method comprising: providing a graphical user interface by which a user groups patient cases into clinically related groups, the graphical user interface graphically representing patient cases by patient case icons comprising patient images or thumbnail images generated from patient images; determining probative features of the patient cases having values that correlate with the clinically related groups; and automatically providing clinical support decision information based on received current patient data relating to a current patient case based on values of the probative features determined from the received current patient data.

In accordance with another disclosed aspect, a storage medium is disclosed, the storage medium storing instructions executable by a digital processor to perform the clinical decision support (CDS) method set forth in the immediately preceding paragraph.

One advantage resides in providing patient case groupings determined holistically by a physician or other skilled medical person in order to establish similarity ground truth information for CDS operation.

Another advantage resides in providing a user interface for manual grouping of similar patient cases in which the patient cases are represented by patient icons comprising patient images or thumbnail images generated from patient images.

Another advantage resides in automatically determining image and optionally non-image features correlating with similarity ground truth information.

Further advantages will be apparent to those of ordinary skill in the art upon reading and understanding the following detailed description.

FIG. 1 diagrammatically shows a clinical decision support (CDS) system.

Figure 2:
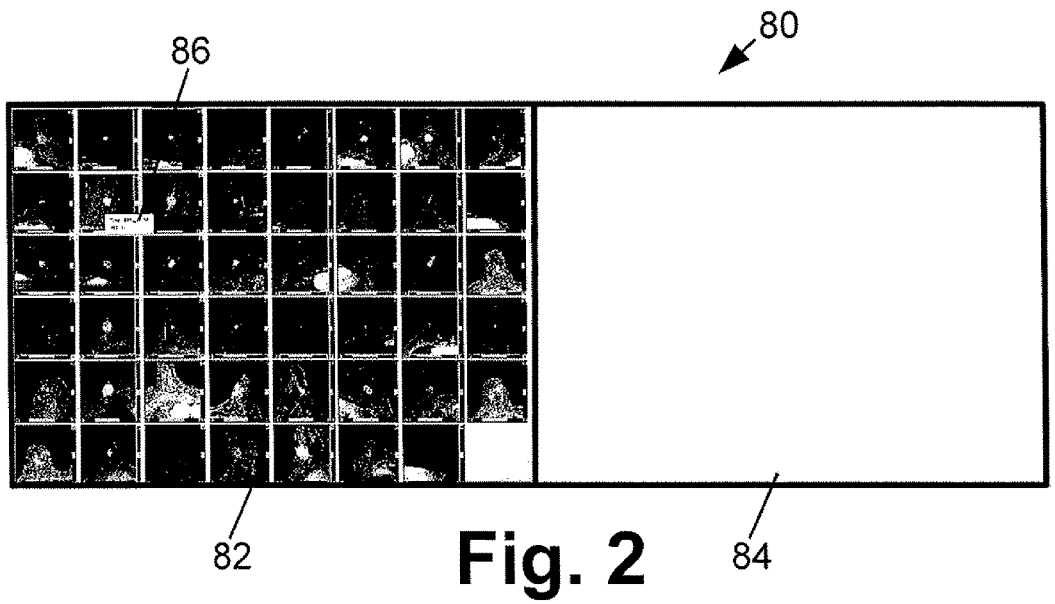
Figure 3:
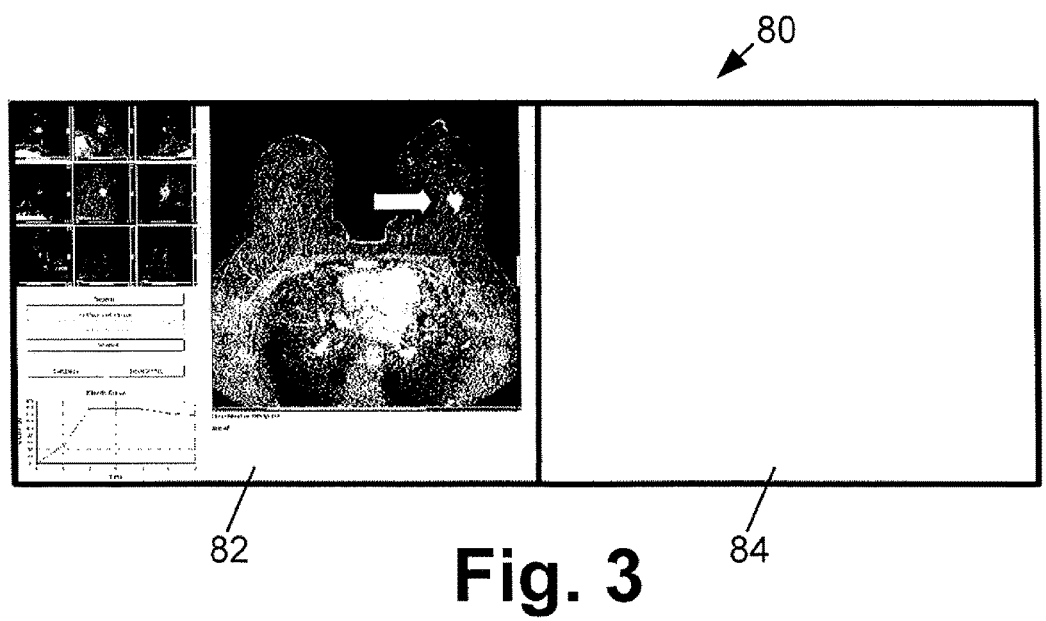
Figure 4:
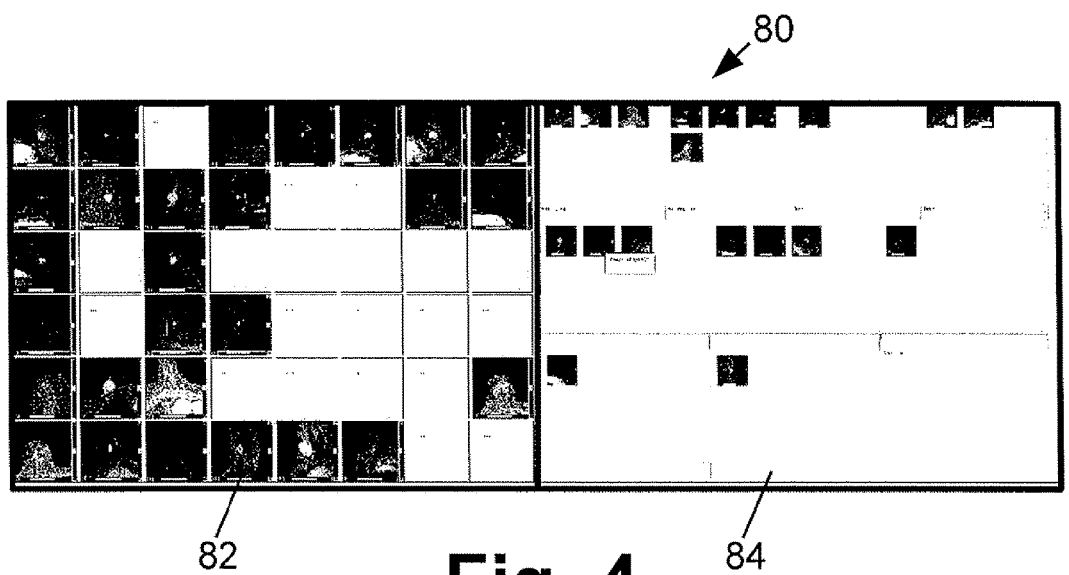

FIGS. 2-4 diagrammatically shows display screenshots of the graphical user interface (GUI) of the case groupings sub-system of the CDS system of FIG. 1.

Figure 5:
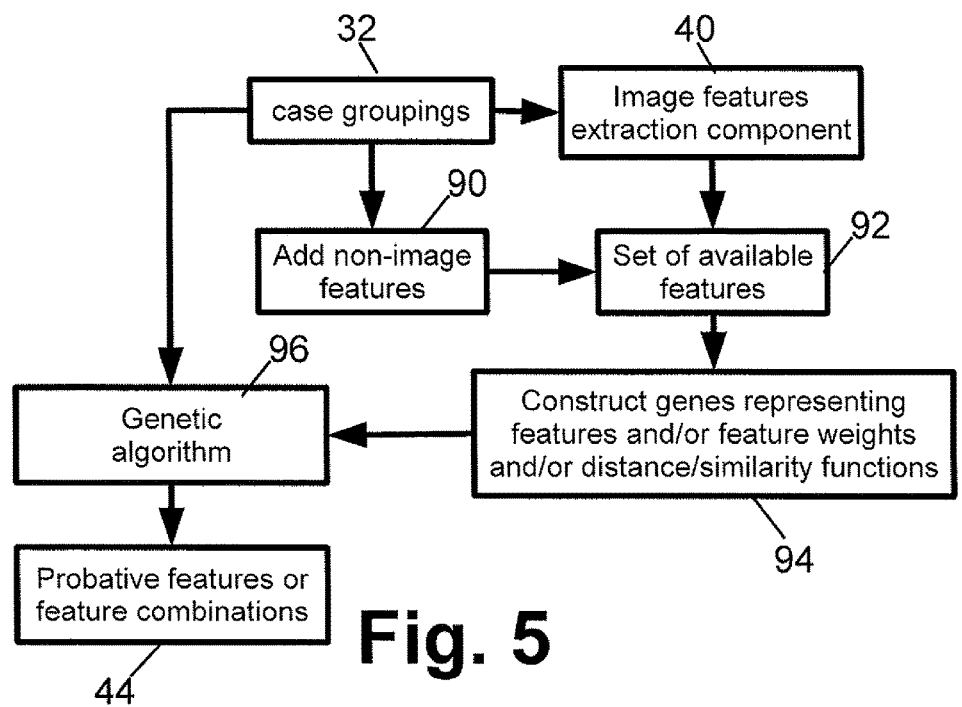

FIG. 5 diagrammatically shows a suitable method performed by the probative features determination sub-system of the CDS system of FIG. 1.

Figure 6:
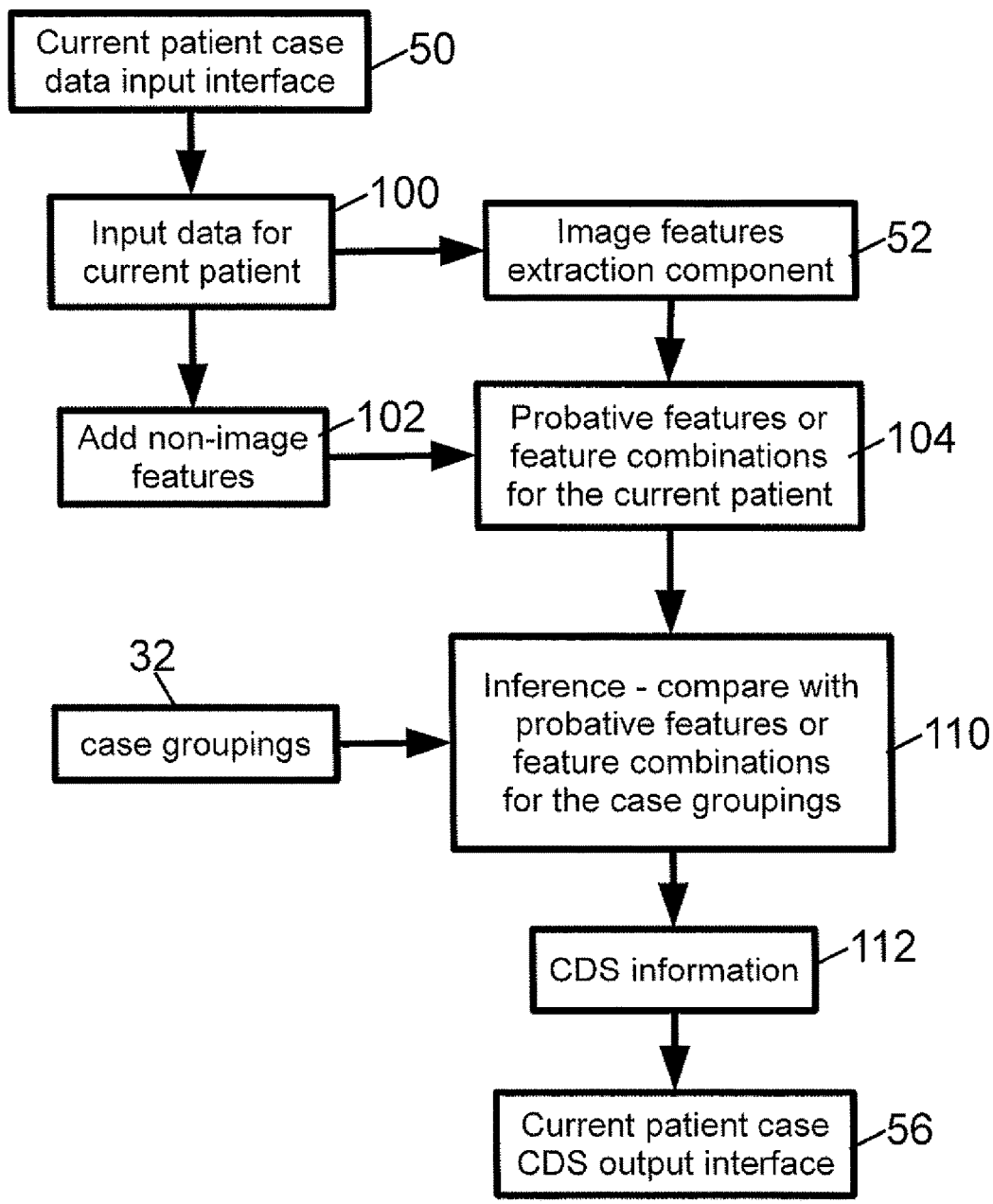

FIG. 6 diagrammatically shows a suitable method performed by the CDS user interface sub-system of the CDS system of FIG. 1.

The present disclosure recognizes that the CDS system operation can be divided into two parts: (i) clustering of similar patient cases in order to identify a similarity "ground truth" (defined below at the end of the next paragraph); and (ii) the identification of probative features for clinical decision support. The present disclosure recognizes that part (i), the clustering of similar patient cases, is not readily automated in a manner acceptable to physicians. Automated machine learning techniques are generally too empirical, have too much potential to produce erroneous clusters, and do not provide a principled decision-making basis. Machine learning approaches also may fail to capture subjective or difficult-to-quantify factors routinely used by physicians in assessing cases and making complex medical diagnoses.

Accordingly, the present application discloses a graphical user interface (GUI) that supports manual grouping of patient cases using a holistic visually-based GUI that concurrently displays more than two patient cases, and preferably a substantial number of patient cases, so as to avoid biases that can be introduced by limited pairwise comparisons. The output of the manual clustering is similarity ground truth information. The information is "ground truth" because the clusters are known or assumed to be correctly grouped because the grouping decisions were made by skilled physicians based on a substantial number of patient cases considered together.

On the other hand, the present disclosure recognizes that part (ii), the identification of probative features, can advantageously be automated using machine learning. The automated identification of probative features can advantageously use as input the accurate similarity ground truth information. Automating part (ii) of the CDS system enhances efficiency and also provides information discovery because correlations between patient cases in the various groups are automatically identified. Such correlations are more likely to be unnoticed by a physician considering at most a few cases at a time. Advantageously, the machine-learned probative features can include non-image features such as patient age, patient gender, patient ethnicity, family medical history, genomic predispositions, and so forth.

With reference to FIG. 1, a clinical decision support (CDS) system includes a patient case grouping sub-system 10 and a probative features determination sub-system 12 that are operative to generate a CDS database 14 that is accessed by a CDS user interface sub-system 16 to provide clinical support decision information. The patient case grouping sub-system 10 operates on contents of a database 20 of patient cases. The patient cases are preferably anonymized by removing identifying information such as proper names, addresses, and so forth so as to comply with applicable privacy laws and standards. The database 20 of patient cases may be derived from contents of a hospital information network (not shown), and the data of the patient cases includes patient images acquired through one or more medical imaging modalities, such as one or more of: computed tomography (CT) imaging; magnetic resonance (MR) imaging; positron emission tomography (PET) imaging; single photon emission computed tomography (SPECT) imaging; fluoroscopy imaging, ultrasound imaging, x-ray imaging; and so forth. By way of example, patient images are optionally stored in a dedicated picture archiving and communications system (PACS) 22 which stores medical patient images along with metadata such as information pertaining to medical imaging modality, resolution or other image acquisition parameters, acquisition time stamps, and so forth.

The patient cases are initially processed by a case grouping graphical user interface (GUI) 30 of the case grouping sub-system 10 that is operative to simultaneously display data relating to more than two different patient cases, for example represented as patient icons comprising patient images or thumbnail images generated from patient images. The term "thumbnail image" represents a reduced-resolution image generated by downsampling a higher-resolution image. By way of example, the thumbnail images are optionally of a standardized size and/or standardized aspect ratio (for example, all being 128×256 pixel images). The thumbnail images are optionally also "simplified" in other ways as compared with the source image, such as for example by converting a color image to a grayscale thumbnail image. By another exemplary option, the thumbnail images may be replaced by or augmented with non-image information, such as a summary block of text or a graphical representation of clinical data (e.g., graphs such as a line graph of blood pressure over time or the kinetic curves used in the analysis of MRI scans, or different types of plots such as a bar graph of a series of different measurements for each patient, such as age, height, weight, etc).

By concurrently displaying information for a substantial number of patient cases, the GUI 30 avoids imposing pairwise comparisons between pairs of patient cases on the user which could disadvantageously lead to biased groupings. However, it is contemplated for the GUI 30 to enable the user to select individual patient cases for more thorough review, for example by displaying non-image patient case information upon suitable selection via the GUI 30 of a particular patient case. The GUI 30 is further configured to enable a user to group the different patient cases represented by the simultaneously displayed data into clinically related groups as determined by the user. The user is preferably a physician or other skilled human medical diagnostician, or a plurality of physicians or other skilled human medical diagnosticians, who generate(s) clinically related groups. For example, the grouping of patient cases into clinically related groups can be performed by a single user (e.g., a single authoritative physician) or can be established as a consensus among a committee or other group of authoritative physicians or other authoritative medical personnel. The patient cases of a clinically related group are considered by the physician who generates the group to have a medical relationship such that a same or similar medical regimen is expected to be applicable to the patient cases in the group. For example, a clinically related group may comprise a group of patient cases in which all patients suffer from a same or similar type of cancer or other same or similar type of medical condition. Resulting case groupings 32 are suitably stored in the CDS database 14. Optionally, the case grouping sub-system 10 further includes a case groupings report generator 34 that generates a human-readable report of the case groupings to provide a written record of the clinically related groups, or for optional review by other physicians or other skilled human medical diagnosticians, or for other purposes.

The clinically related groups 32 are assumed to be correct, that is, are assumed to correctly group patient cases exhibiting a medically significant relationship entailing a same or similar medical regimen. This assumption is likely to be valid since the clinically related groups 32 were generated by a physician or other skilled human medical diagnostician, or by a plurality of physicians or other skilled human medical diagnosticians, based on a substantial number of patient cases presented by the GUI 30 in a holistic fashion. On the basis of this assumption, the clinically related groups 32 are therefore understood to represent the similarity ground truth for the cases in the database 20. Because the grouping was performed manually, the case grouping sub-system 10 provides no express information as to the basis or rationale for the patient case groupings. Indeed, the physician or other skilled human medical diagnostician or plurality of physicians or other skilled human medical diagnosticians may have employed various objective and subjective considerations in generating the patient case groupings.

Although the bases used by the human diagnosticians in grouping together the various clinically related groups 32 may not be readily available, it is reasonable to expect that the clinically related groups 32 have some objectively definable similarities or correlations, and that these objective similarities or correlations are latent information contained in the clinically related groups 32.

Accordingly, the probative features determination sub-system 12 analyzes the clinically related groups 32 to identify probative features that correlate with the various groups. Toward this end, an image features extraction component 40 extracts quantitative image features that have reasonable likelihood of correlating with clinically significant aspects of the patient cases. Some illustrative examples of suitable quantitative image features include tumor size, tumor aspect ratio, tumor tissue density as reflected by image intensity in the tumor region, and so forth. Optionally, the image features extraction component 40 may be user-interactive—for example, the image features extraction component 40 may display a medical patient image and request that the user identify or delineate a tumor in the image using a mouse pointer or other user input mechanism. Additionally or alternatively, the image features extraction component 40 may employ automated tumor identification or other automated or semi-automated medical image analysis. In addition to image features, the probative features determination sub-system 12 may consider non-image features such as patient age, patient gender, patient ethnicity, family medical history, genomic predispositions, and so forth, such information being provided in or derived from the patient cases database 20.

An available feature may or may not be probative. That is, an available feature may correlate with one or more of the patient case groups 32, in which case the feature is a probative feature, or the feature may have little or no correlation with any of the patient case groups 32, in which case it is not probative. Features may also be probative in combination—for example, the features of tumor size and tumor aspect ratio, each standing alone, may have little correlation with any of the patient case groups 32; whereas, the combination of tumor size and tumor aspect ratio together may correlate with one or more of the patient case groups 32.

A machine learning component 42 processes the available features to identify probative features or feature combinations 44 that correlate with one or more of the patient case groups 32, and these probative features or feature combinations 44 are also stored in the CDS database 14. The machine learning component 42 can employ any machine learning technique for identifying such correlations. In some illustrative examples set forth herein, the machine learning component 42 employs a genetic algorithm. Optionally, the machine learning component 42 also identifies the strength of correlation of a probative feature with the patient case groups 32 and assigns feature weights 46 that reflect the strength of correlation. Optionally, the machine learning component 42 also identifies combinations, or weighted combinations, of probative features that correlate with the patient case groups 32, and stores these combinations or weighted combinations as distance or similarity metrics 48. Optionally, the identified probative features information 44, 46, 48 are presented to the user for review, for example by the case groupings report generator 34 or by another reporting tool. Optionally, the user can modify, delete, or otherwise adjust the probative features information 44, 46, 48 based on the user's medical diagnostic expertise.

The user who generates the patient case groupings 32 with the assistance of the case groupings sub-system 10, and who optionally reviews the probative features information 44, 46, 48, is preferably a physician or other skilled human medical diagnostician, or a plurality of physicians or other skilled human medical diagnosticians, who is or are particularly skilled in the medical diagnostic arts. For example, this user or users may include one or more senior physicians or medical specialists having extensive knowledge and skill in the relevant medical area or areas. These users may be specialists, such that for example the cardiac patient cases are grouped by one or more senior cardiac specialists, while the cancer patient cases are grouped by one or more oncology specialists, and so forth. The populating of the CDS database 14 is generally performed prior to the use of the CDS system for clinical decision support operations, although as disclosed herein occasional ongoing updates of the CDS database 14 are also contemplated.

Once the CDS database 14 is populated, the contents of the CDS database 14 are used by the CDS user interface sub-system 16 to generate clinical decision support information for presentation to a user. That is, clinical decision support operations are performed by the CDS user interface sub-system 16 with reference to the CDS database 14. A human user, or plurality of human users, interact with the CDS user interface sub-system 16 to request clinical decision support information for current patient cases. The user of the CDS user interface sub-system 16 is typically a physician or other medical person or plurality of medical persons. However, the user of the CDS user interface sub-system 16 is not necessarily a senior physician, specialist, or other highly skilled medical diagnostician. Rather, the user of the CDS user interface sub-system 16 may be an ordinary physician of ordinary skill who utilizes the CDS user interface sub-system 16 to obtain assistance in making clinical decisions. In general, the user of the CDS user interface sub-system 16 may be a physician or other medical personnel of substantially any skill level.

The CDS user interface sub-system 16 includes a current patient case data input interface 50 via which a user inputs relevant information about a current patient case for which the user seeks clinical decision support. The provided current patient case information may include image data such as patient images, and optionally may also include non-image information such as patient age, patient gender, patient ethnicity, family medical history, genomic predispositions, and so forth. Patient images are processed by an image features extraction component 52 (which may optionally be embodied in common with the image features extraction component 40 of the probative features determination sub-system 12) to extract probative image features. The probative image features, together with any probative non-image features provided via the current patient case data input interface 50, serve as inputs to a clinical decision support inference engine 54 that considers correlations between values of the probative features of the current patient case and values of probative features of the cases of the various patient case groupings 32. By identifying common correlations, the inference engine 54 associates the current patient case with one of the patient case groupings 32. A current patient case CDS output and user validation interface 56 provides the user with clinical decision support information based on the results of the inference engine 54. For example, the clinical decision support information may include: identification of the patient case group most strongly associated with the current patient case; identification of the medical condition of that group with the proposal that the current patient may also have that medical condition; presentation of one or more similar cases extracted from the patient case group most strongly associated with the current patient case; presentation of a proposed medical regimen corresponding to a medical regimen applied in patient cases of the patient case group most strongly associated with the current patient case; or so forth.

Optionally, the current patient case CDS output and user validation interface 56 also provides a user validation function in which the user accepts, rejects, or optionally modifies the presented clinical decision support information. In this case, the user validation information is optionally used by a CDS update sub-system 60 to assess and optionally update the CDS database 14. For example, in one approach the current patient case along with the medical diagnosis of the user (which may either agree with or disagree with the clinical decision support information provided by the CDS user interface sub-system 16) is stored together with similar results for other "current" patient cases so as to provide an update or augmentation of the original patient cases database 20. Occasionally, the updated or augmented collection or database of patient cases is again processed by the CDS database content generation components 10, 12 to update or augment the CDS database 14. In an alternative, computationally less intensive, approach, the current patient case is added to the patient case group of the case groupings 32 if the user agrees that the current patient case does indeed belong with that patient case group. This can be done, for example, by providing the user with a GUI dialog box asking "Add current patient case to the <<< >>> group?" where "<<< >>>" is the identification of the patient case group indicated by the CDS system as matching the current patient case.

The CDS system of FIG. 1 can be implemented in various ways. In the illustrated embodiment, a computer 70 includes a display 72 for displaying visual or graphical output of the components 30, 56, for displaying dialog boxes, windows, or the like of the user input component 50, and so forth. The computer 70 also includes an illustrated keyboard 74, mouse 76, and/or other user input device or devices for receiving user inputs, and still further includes a digital processor (not shown) and one or more storage media (not shown, but suitably embodied for example by a magnetic hard disk drive, an optical disk drive, a random access memory (RAM), a read-only memory (ROM), or so forth). The digital processor executes instructions of a computer program or computer code stored by the one or more storage media in order to implement the processing components 10, 12, 16 of the CDS system, and the CDS database 14 is suitably stored on one or more storage media of the computer 70 or on a remote storage medium accessed via a hospital digital network. In other contemplated embodiments, the processor embodying the processing components 10, 12, 16 may be disposed with or part of a remote server logically disposed on the hospital digital network, and the illustrated computer 70 provides the interfacing hardware 72, 74, 76. In yet other contemplated embodiments, the interfacing hardware may be embodied by a physician's personal data assistant (PDA), cellular telephone, or other portable electronic device with a digital processor.

Having provided an overview of the illustrative CDS system of FIG. 1 which serves as an illustrative example herein, some additional or alternative aspects, and other disclosure are set forth.

In some illustrative embodiments set forth herein, the CDS system and corresponding CDS methods are described in the context of an illustrative breast cancer diagnostic application based on dynamic magnetic resonance imaging (MRI) and additional non-image clinical information. It is to be understood that this is merely an illustrative application and an illustrative imaging modality, and that the disclosed CDS systems and CDS methods are generally applicable to substantially any medical diagnostic application employing substantially any imaging modality that is probative for the medical application to which the CDS system or method is directed.

Each patient case in the database can include multiple, different imaging studies from the same modality or different modalities. Furthermore, for each case, different views of these studies can be stored, or could be derived by image processing. Still further, a given patient case may in some cases be an amalgam or combination of images or other data acquired from two or more similar patients. The imaging studies stored for each patient case in the database can in general be acquired by one or more single imaging modalities, such as x-ray, ultrasound, MR, CT, and so forth, or by multiple imaging modalities for a single patient, such as x-ray mammography, ultrasound, MR breast studies. The imaging studies optionally include time series. For example, for a breast cancer case different dynamic contrast enhanced MR image series may be acquired. Thus, for each patient, the database can store pre-contrast (before the contrast agent administered to the patient), and multiple post-contrast studies, which are acquired at different time instants after the contrast agent has been administered. The database can also include derived sequences, such as multiple subtraction series, which are the subtraction of a pre-contrast study from different post-contrast series. The database optionally also includes derived image sequences representing the abnormalities and surrounding areas, e.g., volume of interests (VOI) for such variations. The database 20 optionally further includes non-image based clinical information besides the imaging studies. Non-image data may include, for example, demographics information such as gender, age, ethnicity, personal medical history of the patient, family history, chief complains, genomic predispositions (e.g. in breast cancer BRCA1 and/or BRCA2 positive), and other risk factors. The database 20 suitably employs a hierarchical database model, a relational model by applying the SQL technique, or another suitable database configuration.

With reference to FIG. 2, the interactive case grouping graphical user interface (GUI) 30 displays data representing multiple patient cases on a display 80. A lefthand window 82 displays data representing ungrouped patient cases, while a righthand window 84 displays data representing grouped patient cases. The righthand window 84 is empty in FIG. 2, indicating that no patient cases have yet been sorted into groups. It is to be understood that the display 80 may include two or more display devices, such as two or more computer monitors, and the designation of "left" or "right" is arbitrary. For example, in some embodiments two computer monitors are provided—one monitor displays the window 82 showing ungrouped patient cases, while the other monitor displays the window 84 showing grouped patient cases. In the illustrative embodiments, the displayed representative data comprises a patient image or a thumbnail image generated from a patient image to represent each patient case. In other words, a patient image or corresponding thumbnail image serves as a patient icon for the graphical sorting process. Preferably, the displayed image represents the volume of interest (VOI) containing a clinical abnormality of interest. In the illustrative example of FIG. 2, the representative images are VOIs which are derived as subtraction series (that is, $2^{nd}$ post-contrast—pre-contrast T1—weighted MRI studies) and show breast lesions.

Optionally, non-image data is also displayable. For example, FIG. 2 shows a "pop-up window" 86 showing non-image data such as "Age: 47" for a patient case responsive to the mouse or other pointer hovering over the representative patient icon. The pop-up window can be a temporary window that disappears once the mouse pointer is moved away, or can be a persistent window that remains open until it is closed. In some embodiments, hovering the mouse produces a temporary window with limited non-image information, while a positive user action such as clicking on the patient icon using the mouse 76 produces a persistent window containing more information. In addition to showing non-image data, these approaches can additionally or alternatively be used to show image metadata such as acquisition timestamp, resolution, or so forth.

With reference to FIG. 3, a positive user action such as clicking on the patient icon using the mouse 76 may also optionally bring up more complete information. In FIG. 3, such an action causes more complete information about the selected patient case to be displayed so as to wholly occupy the lefthand window 82. Optionally, both windows 82, 84 can be used for this purpose, or a separate (i.e., third) window can be displayed to contain this information. This optional display mode enables the user to more closely evaluate the selected patient case. In the example shown in FIG. 3, this mode displays for a breast cancer case a relevant dynamic contrast enhanced MR imaging study. It this example, the lefthand window 82 displays a bilateral view of the breast and an arrow pointing to the abnormality for easy identification. The arrow is suitably generated based on metadata identifying the abnormality stored in the PACS 22. Optionally, the GUI 30 is configured to enable the user to selectively change views among different imaging studies of the clinical case. For breast MR imaging studies, for example, the user can optionally switch among pre-contrast, different post-contrast series, different acquisition series e.g. T2-weighted sequences, or derived sequences, such as subtraction series. For each series the user may optionally be able to change the window or level setting to have optimal view for the particular series and for different users. Kinetic curves can be displayed representing the uptake of the contrast agent in the abnormalities over time, as shown for example in the lower lefthand corner of the window 82 in FIG. 3. The upper left corner of this view also shows the neighbouring eight cases to be sorted and they are represented by the VOIs. The VOI in the middle is the case which whole breast view is shown on the right side. Under the bilateral view of the breast, the clinical information is displayed. Optionally, additional windows, parts of the monitor, or additional monitors can have the same functionality to show other clinical cases. For example, in some embodiments the two windows 82, 84 may be selected by the user to display two patient cases in more detail for convenient visual comparison.

With reference to FIG. 4, a screenshot is shown of the case grouping GUI 30 being used to create clinically related groups as selected by the user. The user employs a drag-and-drop mechanism in which the patient case icons are dragged from the lefthand window 82 into a region of the righthand window 84 representing the group. To create a group, a patient case icon is dragged from the lefthand window 82 into an undesignated region of the righthand window 84 that defines a new group creation region. As the patient case icon is dropped into the new group creation region, a similarity group is created including that patient case. Optionally, the groups can be labeled or otherwise annotated by the user to indicate the basis of clinical relation of the patient cases in the group, or to provide other useful information. Optionally, the sub-window for a group may include scroll bars to accommodate more patient cases than can be displayed simultaneously, and/or can incorporate features such as zooming or panning through the use of keyboard, mouse, or other interaction devices. Optionally, a patient case can be moved from one group to another in accordance with a patient case reallocation decision by the user. Optionally, a patient case can be removed from any of the existing groups and replaced amongst the set of cases that have not yet been grouped, i.e. the lefthand window 82. The drag-and-drop operations can be implemented using the mouse 76, or by using the keyboard 74 (for example, tabbing through the various windows and sub-windows), or by other user interfacing operations. Still further, GUI manipulations such as lassoing and the like can be used to implement the grouping operations.

In the arrangement shown in FIG. 4, each patient case is assigned exclusively to a single group of clinically related cases. In view of this, the patient case icon is removed from the lefthand window 82 when it is dragged-and-dropped into one of the groups in the righthand window 84, which is why the grid of patient case icons shown in the lefthand window 82 of FIG. 4 has numerous gaps. In an alternative embodiment, each patient case may optionally be assigned to two or more groups of clinically related cases. For example, a single patient case may be assigned to a group having as its clinical relationship a particular tumor characteristic, and may also be assigned to a group having as its clinical relationship image evidence of a certain level of metastasis. In this alternative embodiment, the patient case icon may be retained in the lefthand window 82 after being moved into a group on the righthand window 84, so as to continue to be available for inclusion in other groups of clinically related cases.

Once the user has completed allocation of patient cases into clinically related groups, for example as described with reference to FIGS. 2-4, the case groupings report generator 34 is optionally invoked to generate a human-readable report describing the similarity groups. The report can, for example, be a free text report or a structured spreadsheet-based report. The description in the report of a clinically related group may include, for example: a group name; an identification of the cases contained in the group by subject ID (preferably anonymized), study ID, or so forth; a textual description of the group entered by the user; or so forth. A similarity group identifier is assigned to each case in the internal representation of the data.

In some embodiments, once a patient case icon has been dropped into a similarity group, the group identifier of the patient case is set to the identifier of that group. Thus, on report generation it is straightforward to determine the number of similarity groups. Once the total number of groups has been established the report generator 34 loops through each group, finding the patient cases in that group and writing the relevant information into the report. Optionally, the report generator 34 can also generate an intermediate report, without sorting all of the patient cases into similarity groups.

With reference to FIG. 5, the similarity ground truth quantified by the clinically related groups 32 are processed to identify relevant (that is, probative) perceptual and clinical features distinguishing the groups from each other are obtained. In the illustrative embodiment, the probative features are obtained by an optimization of the selection of probative features respective to the case groupings 32, suitably performed by applying image processing and machine learning techniques. This translates the similarity sense of the physician captured by the groupings 32 defining the similarity ground truth into optimal computer—identified probative features. These probative features can then be used to represent patient cases in the CDS system. Optionally, an optimal distance or similarity metric is determined by machine learning techniques using the similarity ground truth as training data. As shown in FIG. 5, the images of the case groupings 32 are processed by the image features extraction component 40 to identify image features. Optionally, non-image features are added 90 to generate a set of available features 92. A given available feature may or may not be probative, in that it may or may not be useful for discriminating amongst patient cases of the groups 32. Then, using machine learning techniques feature selection is applied to find the probative feature set, and optionally to further find a distance or similarity metric employing the probative features.

In the illustrative embodiment of FIG. 5, the machine learning employs a genetic algorithm coupled with k-mean clustering, and uses the established similarity clusters as ground truth. Genetic algorithms (GA) are useful for optimizing problems in high-dimensional spaces, and have been found to be useful in combinatorial problems such as feature selection. In GA-based feature selection, different feature subsets are encoded on a series of "chromosomes". A population of different chromosomes evolves through a process of mating (swapping features), reproduction, and mutation. Selection pressure is exercised such that the fittest chromosomes, as measured by a suitable fitness criterion, have the greatest chance to pass on their genetic information. The population thus evolves towards feature subsets that are optimal with respect to an objective function referred to as the fitness function or fitness criterion.

In some embodiments for finding the optimal feature subset and distance metric, genetic algorithms are coupled with k-nearest neighbor classification and using the established similarity clusters as ground truth. The genetic algorithm iteratively identifies candidate feature subsets, which are evaluated via a fitness function. Non-image-based clinical information are optionally added to the feature pool, for example using a scaling method of 1-of-C in order to scale with the image features.

Chromosomes are constructed 94 which represent available features. For example, each available feature can be represented by a binary gene of the chromosome, in which a binary value of "1" indicates the feature is a probative feature and a binary value of "0" indicates the feature is not probative. In a typical genetic algorithm, a substantial set (that is, "population") of chromosomes are generated with different genes randomly or pseudorandomly turned "on" (that is, having value "1" indicating the feature is probative) or "off" (that is, having value "0" indicating the feature is not probative). A genetic algorithm 96 is then iteratively applied using as the selection algorithm correlation with the case groupings 32 and incorporating random or pseudorandom gene mutation algorithms in order to optimize or "evolve" the chromosome population respective to correlation with the patient case groupings 32. The "on" genes or combinations of "on" genes of the chromosomes of the evolved population then define the probative features or feature combinations 44.

Optionally, the genes may have continuous values indicative of the strength of correlation of the corresponding features with the case groupings 32, rather than having binary gene values. In these embodiments, the genetic algorithm evolves the weights of the genes of the chromosome population, so that the genes of the evolved population provide correlation weights for the probative features. In some such embodiments, the combination of weights that best correlates with the patient case groupings 96, as represented by the combination of genes in the surviving evolved chromosomes, can also be used to define a distance or similarity metric.

For example, as the first step of one iteration of the genetic algorithm 96, one patient case can be left out and distances are calculated between that patient case and all of the other cases using the features represented in the chromosome. The fitness function of the genetic algorithm 96 can be determined as a function of these distances and the similarity groups to which the patient cases belong (e.g., by ranking the distances from the shortest to the longest, how many distances do not belong to the left out patient case's own similarity group). This can be done for each patient case in the groups 32, and an accumulated fitness value is derived. Then, the chromosomes are modified or "mutated" in a random or pseudorandom fashion as per the principle of the chosen genetic algorithm 96.

In another embodiment, the genetic algorithm is constrained to always turn a certain group of features on or off together, such as may be dictated by a physician or other human medical diagnostician who knows that these features are related. In these embodiments, the construction of the chromosomes in operation 94 can be performed in the following illustrative manner: a gene represents an available feature and genes which attempt to measure the same conceptual feature category are grouped together. In this manner the genetic algorithm 96 is constrained such that the genetic algorithm never lets all of the genes representing the calculated measures for an aspect such as spiculation (for example) be discarded in total. That is, the genetic algorithm is constrained such that at least one spiculation feature or gene is always present in a chromosome since spiculation is known by human physicians to be a probative feature for breast cancer diagnoses.

In other embodiments, the type of distance metric (for example, a Euclidean distance, or a Mahalanobis or city block, or so forth) can be chosen by the genetic algorithm 96 by including genes representing the different distance functions.

While the illustrative example of FIG. 5 employs a genetic algorithm for the machine learning component 42, this is merely an illustrative example. In general, the machine learning component 42 can employ substantially any machine learning method or combination of methods, including as some other illustrative examples: simulated annealing; exhaustive searches; floating searches; principle component analysis (PCA) or other feature reduction methods; or so forth. Moreover, it is contemplated to omit the machine learning component 42 and to configure the probative features determination sub-system 12 to provide a graphical user interface that enables a physician or other human medical diagnostician, or a plurality of such physicians or other human medical diagnosticians, to select the probative features manually based on observations of the available features of the patient case groups 32. For example, the list of probative perceptual and clinical features can optionally be obtained manually from the physician using cognitive methods. As a specific example, in a breast cancer application based on dynamic contrast enhanced MR imaging, the morphological features of the abnormalities and the surrounding areas, such as shape, margin, texture, kinetic curves, or so forth, may be calculated in various ways by image processing techniques, and examined for probativeness by the physician. The physician knows, for example, that spiculation is a probative feature for breast cancer diagnoses, and so the physician is likely to consider different spiculation measures as candidate probative features. By examining values of the different spiculation measures amongst the patient cases of the patient case groups 32, the physician can manually select those spiculation measures that most strongly correlate with the groupings 32 as probative features. Manual cognitive analysis techniques can also be advantageously combined with machine learning approaches. For example, cognitive analysis can be used to generate a set of "candidate" probative features, followed by PCA or another features reduction method to reduce the number of probative features.

With reference to FIG. 6, an illustrative operation of the CDS user interface sub-system 16 is described. The current patient case data input interface 50 is accessed by a user to input data for a current patient 100. The input current patient data 100 generally includes one or more patient images, such as images of the patient acquired by one or more of: CT imaging, MR imaging, PET imaging, SPECT imaging, fluoroscopy imaging, ultrasound imaging, and x-ray imaging. The image features extraction component 52 processes these current patient images to extract probative image features, and optionally probative non-image features 102 are combined with the probative image features to define a set of probative features or feature combinations for the current patient case 104. As noted earlier, the image features extraction component 52 may optionally be embodied by the same component embodying the image features extraction component 40 of the probative features determination sub-system 12.

An inference operation 110 is performed by the CDS inference engine 54 in order to generate clinical decision support information 112 that is presented to the user via the current patient case CDS output interface 56. The CDS interface engine 54 can be variously embodied. In some embodiments, the distance or similarity metric or metrics 48 are used to quantify the distance (or, analogously, to quantify similarity) of the current patient case respective to each case in each group of clinically related cases of the groupings 32. For a distance metric, the inference employs the following relation:

$$G_{match} = \min_g \{d(c, g)\},$$

where d(c,g) represents the average value of the distance metric d for the current patient case denoted c from the cases that comprise a group denoted g, the operator $$\min_g \{\ldots\}$$

denotes the minimum over all groups g of the groupings 32, and $G_{match}$ represents the group at minimum distance (and hence, the group most similar to the current patient case c). For a similarity metric s, the analogous expression is:

$$G_{match} = \max_g \{s(c, g)\}.$$

Other inference algorithms can also be used, such as a trained classifier that receives as inputs the probative features of the current patient case and outputs the most closely matching group. Such a trained classifier can be trained, for example, using a training set of patient cases pre-annotated with the group identifications, as in the groupings 32. In some embodiments, a k-nearest neighbour (k-NN) classifier is used, which provides an estimate of the posterior probability that a query case belongs to a patient case grouping. Based on the k most similar retrieved cases (shortest distances, in the case of a distance metric), this posterior probability is estimated by the number of cases of the patient case grouping in the k most similar cases divided by k. This is merely an illustrative example, and other classifiers can be used.

The following describes further aspects of a proposed embodiment directed to diagnosing breast cancer. Presently, breast cancer is the most common cancer and the second most common cause of cancer death among women in the United States. CDS systems and methods based on content-based image retrieval (CBIR), as disclosed herein, mimic natural physician reasoning by retrieving similar cases that resemble previously reviewed and diagnosed patient cases. These methods rely on collected past experience and offer additional knowledge, such as automated identification of correlated probative features, to support physician decision-making. Therefore, the disclosed content-based CDS system for breast cancer diagnosis helps physicians to decide whether a queried case is likely to be malignant or benign, thus avoiding misinterpretation and preventing unnecessary biopsies. While dynamic contrast-enhanced MRI (DCE-MRI) has emerged as a main diagnostic tool for breast lesion characterization due to its superior sensitivity, it often leads to a high incidence of negative biopsies. The probative features determination sub-system 12 including a machine learning component 42, as disclosed herein, translates the physician's (or physicians') subjective sense of patient case similarity as reflected in the case groupings 32 into probative features 44 optionally including automatically computable metrics 46, 48.

A CDS system based on CBIR, as disclosed herein, which is optimized on clinical similarity for breast cancer DCE-MRI studies is expected to substantially improve physicians' diagnostic accuracy and is expected to reduce both unnecessary biopsies and delays in treatment. A content-based retrieval based on morphological and kinetic features extracted from DCE-MRI breast studies can retrieve prior cases with the same diagnosis and similar imaging characteristics as the query case. The disclosed CDS systems and methods enable grouping based on clinical similarity of breast cancer cases using the expertise of expert physicians. Probative image features and non-image features are identified based on cognitive analysis or other techniques for correlating features with the case groupings. By integrating advanced computer vision, image processing and machine learning techniques the CBIR-based CDS system is developed and optimized for the application of breast cancer diagnosis so as to substantially mirror the similarity judgments made by human physician experts. While using breast cancer diagnosis as an illustrative application, it will be appreciated that the underlying methodology can be generalized and adapted to other solid tumors, such as colon, lung, liver, brain cancer, and for diagnosis of other types of medical maladies, both in and outside of oncology.

This application has described one or more preferred embodiments. Modifications and alterations may occur to others upon reading and understanding the preceding detailed description. It is intended that the application be construed as including all such modifications and alterations insofar as they come within the scope of the appended claims or the equivalents thereof.

Having thus described the preferred embodiments, the invention is now claimed to be:

1. A clinical decision support (CDS) system comprising:
a case grouping sub-system including a graphical user interface that simultaneously displays data representing a plurality of patient cases and receives from a user a selection of patient cases represented by the simultaneously displayed data to form each of a plurality of user-defined clinically related groups;
a probative features determination sub-system that determines probative features that distinguish among the clinically related group using a machine learning component that implements an algorithm or combination of algorithms selected from a group consisting of: a genetic algorithm, a k-nearest neighbor algorithm, a k-mean clustering algorithm, a simulated annealing algorithm, an exhaustive search algorithm, a feature reduction algorithm, and a floating search algorithm;
a CDS user interface that receives current patient data relating to a current patient case; and
a CDS inference engine that:
identifies a select clinically related group based on values of the probative features determined from the received current patient data;
determines clinical decision support information based on one or more treatments associated with the select clinically related group; and
provides the clinical decision support information to the user for prescribing to the current patient,
wherein the clinical decision support information includes a medical regime to be applied corresponding to a prior medical regime of one or more prior patient cases having values of probative features most closely related to the values of the probative features determined from the current patient data.

2. The CDS system of claim 1, wherein the case grouping sub-system provides drag-and-drop case grouping in which the user drags displayed data representing a patient case from a source visual display region to a region representing the clinically related group.

3. The CDS system of claim 2, wherein the case grouping sub-system provides a drag-and-drop grouping in which a user drags displayed data representing a patient case from a source visual display region to a new group creation region to create an other clinically related group.

4. The CDS system of claim 1, wherein the displayed data representing a patient case comprises a patient image or a thumbnail image generated from a patient image.

5. The CDS system of claim 4, wherein the patient image includes one or more of: a computed tomography (CT) image, a magnetic resonance (MR) image, a positron emission tomography (PET) image, a single photon emission computed tomography (SPECT) image, a fluoroscopy image, an ultrasound image, and an x-ray image.

6. The CDS system of claim 1, wherein the case grouping sub-system concurrently displays patient case icons comprising patient images or thumbnail images generated from patient images and enables a user to graphically group selected patient case icons to form the user-defined clinically related group.

7. The CDS system of claim 6, wherein the patient images are one or more of: computed tomography (CT) images, magnetic resonance (MR) images, positron emission tomography (PET) images, single photon emission computed tomography (SPECT) images, fluoroscopy images, ultrasound images, and x-ray images.

8. The CDS system of claim 1, wherein the machine learning component determines the probative features based on values for different patient cases that correlate with the clinically related group related to each patient case.

9. The CDS system of claim 8, wherein the machine learning component determines a distance or similarity function associating the probative features to the clinically related groups.

10. The CDS system of claim 1, wherein the machine learning component determines probative feature weights.

11. The CDS system of claim 1, wherein the probative features determination sub-system includes an image features extraction component that extracts image features from a patient image, the machine learning component operating on at least the image features.

12. The CDS system of claim 1, wherein the inference engine that determines a distance or similarity measure associated with each clinically related group based on values of the probative features determined from the received current patient data and identifies the select clinically related group based on the distance or similarity measure.

13. A clinical decision support (CDS) method implemented by a CDS system, the CDS method comprising:
providing, by a processor of the CDS system, a graphical user interface to a user, the graphical user interface graphically representing patient cases on a display device by patient case icons comprising patient images or thumbnail images generated from patient images;
receiving, from the user via the graphical user interface, a selection of patient cases that form each of a plurality of user-defined clinically related groups;
determining, by the processor, probative features of the patient cases having values that distinguish among the user-defined clinically related groups using a machine learning component that implements an algorithm or combination of algorithms selected from a group consisting of: a genetic algorithm, a k-nearest neighbor algorithm; a k-mean clustering algorithm, a simulated annealing algorithm, an exhaustive search algorithm, a feature reduction algorithm, and a floating search algorithm;
receiving current patient data related to a current patient;
identifying, by the processor, a select clinically related group of the plurality of clinically related groups based on values of the probative features determined from the received current patient data;
determining clinical decision support information for the current patient based on one or more treatments associated with the select clinically related group; and providing the clinical decision support information to the user for prescribing to the current patient;

wherein the clinical decision support information includes a medical regime to be applied corresponding to a prior medical regime of one or more prior patient cases having values of probative features most closely related to the values of the probative features determined from the current patient data.

14. The CDS method of claim 13, wherein the graphical user interface provides drag-and-drop manipulation of the patient case icons by which a user groups patient cases into each clinically related group.

15. The CDS method of claim 13, wherein the graphical user interface displays non-image patient case information responsive to user selection of a patient case icon via the graphical user interface.

16. The CDS method of claim 1, wherein the determining of the probative features includes extracting image features from patient images, the image features being processed by the machine learning component.

17. The CDS method of claim 16, wherein the machine learning component further processes at least some non-image features.

18. A non-transitory computer readable medium that includes instructions executable by a digital processor to:
provide a graphical user interface by which a user groups patient cases into a plurality of user-defined clinically related groups, the graphical user interface graphically representing patient cases by patient case icons comprising patient images or thumbnail images generated from patient images;
determine probative features of the patient cases having values that distinguish among the user-defined clinically related groups using a machine learning component that implements an algorithm or combination of algorithms selected from a group consisting of: a genetic algorithm, a k-nearest neighbor algorithm, a k-mean clustering algorithm, a simulated annealing algorithm, an exhaustive search algorithm, a feature reduction algorithm, and a floating search algorithm;
receive current patient data related to a current patient;
identify a select clinically related group of the plurality of clinically related groups based on values of the probative features determined from the received current patient data,
determine clinical decision support information for the current patient based on one or more treatments associated with the select clinically related group; and
provide the clinical decision support information to the user for prescribing to the current patient;
wherein the clinical decision support information includes a medical regime to be applied corresponding to a prior medical regime of one or more prior patient cases having values of probative features most closely related to the values of the probative features determined from the current patient data.

19. The medium of claim 17, wherein the machine learning component determines a distance or similarity measure associated with each clinically related group based on values of the probative features determined from the received current patient data and identifies the select clinically related group based on the distance or similarity measure.

20. The medium of claim 17, wherein the graphical user interface provides drag-and-drop manipulation of the patient case icons by which a user groups patient cases into each clinically related group.

* * * * *